United States Patent
Augarten (10) Patent No.: US 9,125,718 B2
(45) Date of Patent: Sep. 8, 2015

(54) ELECTRONICALLY ENHANCED ACCESS PORT FOR A FLUID FILLED IMPLANT

(71) Applicant: Apollo Endosurgery, Inc., Austin, TX (US)

(72) Inventor: Mike Augarten, Goleta, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 0 days.

(21) Appl. No.: 13/923,076

(22) Filed: Jun. 20, 2013

(65) Prior Publication Data
US 2013/0281773 A1    Oct. 24, 2013

Related U.S. Application Data

(63) Continuation of application No. 12/873,096, filed on Aug. 31, 2010, now abandoned.

(60) Provisional application No. 61/330,266, filed on Apr. 30, 2010.

(51) Int. Cl.
*A61F 5/00* (2006.01)
*A61M 39/02* (2006.01)
*A61F 2/04* (2013.01)

(52) U.S. Cl.
CPC ............... *A61F 5/0059* (2013.01); *A61F 2/04* (2013.01); *A61F 5/003* (2013.01); *A61F 5/0013* (2013.01); *A61F 5/0056* (2013.01); *A61M 39/0208* (2013.01); *A61M 2039/0226* (2013.01); *A61M 2039/0238* (2013.01);
(Continued)

(58) Field of Classification Search
CPC ..... A61F 5/0059; A61F 5/003; A61F 5/0056; A61F 5/0013; A61F 2/04; A61M 39/0208; A61M 2039/0238; A61M 2039/0226; A61M 2039/0063; A61M 2039/0244; A61M 2205/215; A61M 2205/82; A61M 2205/583; A61M 2210/1053
USPC ........................................................... 600/37
See application file for complete search history.

(56) References Cited

U.S. PATENT DOCUMENTS

| | | | |
|---|---|---|---|
| 586,113 | A | 7/1897 | Bott |
| 2,163,048 | A | 6/1939 | McKee |

(Continued)

FOREIGN PATENT DOCUMENTS

| | | | |
|---|---|---|---|
| CN | 1250382 | A | 4/2000 |
| CN | 1367670 | A | 9/2002 |

(Continued)

OTHER PUBLICATIONS http://en.wikipedia.org/wiki/Injection.sub.—molding. dated: Mar. 20, 2014.

(Continued)

*Primary Examiner* — Jacqueline Cheng
*Assistant Examiner* — Kaylee Wilson
(74) *Attorney, Agent, or Firm* — Gordon & Jacobson, PC (57) ABSTRACT

The present invention provides for an access port configured to detect its tilt within the body to facilitate a physician's access thereto. The access port can include a tilt detector to detect tilt datum, and a display screen to display the tilt of the access port. In addition, the tilt detector and the display screen can indicate whether the access port is flipped or not. The tilt detector can include an accelerometer to aid in determining the tilt of the access port.

21 Claims, 7 Drawing Sheets

(52) U.S. Cl.
CPC ... *A61M 2205/215* (2013.01); *A61M 2205/583* (2013.01); *A61M 2205/82* (2013.01); *A61M 2210/1053* (2013.01)

(56) References Cited

U.S. PATENT DOCUMENTS

| | | |
|---|---|---|
| 2,737,954 A | 3/1956 | Knapp |
| 3,371,352 A | 3/1968 | Siposs |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,731,352 A | 5/1973 | Okamoto |
| 3,840,018 A | 10/1974 | Heifetz |
| 3,958,562 A | 5/1976 | Hakim |
| 3,971,376 A | 7/1976 | Wichterle |
| 4,019,499 A | 4/1977 | Fitzgerald |
| 4,118,805 A | 10/1978 | Reimels |
| 4,151,835 A | 5/1979 | Copeland |
| 4,161,943 A | 7/1979 | Nogier |
| 4,164,943 A | 8/1979 | Hill |
| 4,190,040 A | 2/1980 | Schulte |
| 4,233,992 A | 11/1980 | Bisping |
| 4,265,252 A | 5/1981 | Chubbuck |
| 4,280,722 A | 7/1981 | Guptil |
| 4,413,985 A | 11/1983 | Wellner |
| 4,474,572 A | 10/1984 | McNaughton |
| 4,502,335 A | 3/1985 | Wamstad |
| 4,543,088 A | 9/1985 | Bootman |
| 4,557,722 A | 12/1985 | Harris |
| 4,569,675 A | 2/1986 | Prosl |
| 4,588,394 A | 5/1986 | Schulte |
| 4,592,339 A | 6/1986 | Kuzmak |
| 4,592,355 A | 6/1986 | Antebi |
| 4,634,427 A | 1/1987 | Hannula |
| 4,655,765 A | 4/1987 | Swift |
| 4,673,394 A | 6/1987 | Fenton |
| 4,692,146 A | 9/1987 | Hilger |
| 4,696,288 A | 9/1987 | Kuzmak |
| 4,704,103 A | 11/1987 | Stoeber |
| 4,710,174 A | 12/1987 | Moden |
| 4,738,657 A | 4/1988 | Hancock |
| 4,767,410 A | 8/1988 | Moden |
| 4,772,270 A | 9/1988 | Wiita |
| 4,778,452 A | 10/1988 | Moden |
| 4,781,680 A | 11/1988 | Redmond |
| 4,796,641 A | 1/1989 | Mills |
| 4,802,885 A | 2/1989 | Weeks |
| 4,832,054 A | 5/1989 | Bark |
| 4,840,615 A | 6/1989 | Hancock |
| 4,850,227 A | 7/1989 | Luettgen |
| 4,858,623 A | 8/1989 | Bradshaw |
| 4,861,341 A | 8/1989 | Woodburn |
| 4,881,939 A | 11/1989 | Newman |
| 4,886,501 A | 12/1989 | Johnston |
| 4,902,278 A | 2/1990 | Maget |
| 4,904,241 A | 2/1990 | Bark |
| 4,913,702 A | 4/1990 | Yum |
| 4,915,690 A | 4/1990 | Cone |
| 4,929,230 A | 5/1990 | Pfleger |
| 4,929,236 A | 5/1990 | Sampson |
| 4,959,752 A | 9/1990 | Samarov |
| 4,966,588 A | 10/1990 | Rayman |
| 4,967,755 A | 11/1990 | Pohndorf |
| 4,978,338 A | 12/1990 | Melsky |
| 5,006,115 A | 4/1991 | McDonald |
| 5,013,298 A | 5/1991 | Moden |
| 5,026,344 A | 6/1991 | Dijkstra |
| 5,041,098 A | 8/1991 | Loiterman |
| 5,045,060 A | 9/1991 | Melsky |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan |
| 5,108,377 A | 4/1992 | Cone |
| 5,125,408 A | 6/1992 | Basser |
| 5,133,753 A | 7/1992 | Bark |
| 5,137,529 A | 8/1992 | Watson |
| 5,147,483 A | 9/1992 | Melsky |
| 5,152,747 A | 10/1992 | Olivier |
| 5,167,638 A | 12/1992 | Felix |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber |
| 5,250,026 A | 10/1993 | Ehrlich |
| 5,273,537 A | 12/1993 | Haskvitz |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg |
| 5,337,747 A | 8/1994 | Neftel |
| 5,360,407 A | 11/1994 | Leonard |
| 5,368,040 A | 11/1994 | Carney |
| 5,387,192 A | 2/1995 | Glantz |
| 5,391,164 A | 2/1995 | Giampapa |
| 5,449,368 A | 9/1995 | Kuzmak |
| 5,476,460 A | 12/1995 | Montalvo |
| 5,514,174 A | 5/1996 | Heil |
| 5,540,648 A | 7/1996 | Yoon |
| 5,556,388 A | 9/1996 | Johlin |
| 5,558,641 A | 9/1996 | Glantz |
| 5,562,617 A | 10/1996 | Finch |
| 5,571,104 A | 11/1996 | Li |
| 5,575,777 A | 11/1996 | Cover |
| 5,601,604 A | 2/1997 | Vincent |
| 5,637,102 A | 6/1997 | Tolkoff |
| 5,653,755 A | 8/1997 | Ledergerber |
| 5,658,298 A | 8/1997 | Vincent |
| 5,674,397 A | 10/1997 | Pawlak |
| 5,683,447 A | 11/1997 | Bush |
| 5,688,237 A | 11/1997 | Rozga |
| 5,695,490 A | 12/1997 | Flaherty |
| 5,716,342 A | 2/1998 | Dumbraveanu |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin |
| 5,814,019 A | 9/1998 | Steinbach |
| 5,833,654 A | 11/1998 | Powers |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank |
| 5,932,460 A | 8/1999 | Mills |
| 5,935,083 A | 8/1999 | Williams |
| 5,938,669 A | 8/1999 | Klaiber |
| 5,951,512 A | 9/1999 | Dalton |
| 6,024,704 A | 2/2000 | Meador |
| 6,030,369 A | 2/2000 | Engelson |
| 6,039,712 A | 3/2000 | Fogarty |
| 6,074,341 A | 6/2000 | Anderson |
| 6,090,066 A | 7/2000 | Schnell |
| 6,098,405 A | 8/2000 | Miyata |
| 6,102,678 A | 8/2000 | Peclat |
| 6,102,922 A | 8/2000 | Jakobsson |
| 6,123,700 A | 9/2000 | Mills |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen |
| 6,221,024 B1 | 4/2001 | Miesel |
| 6,234,973 B1 | 5/2001 | Meador |
| 6,258,079 B1 | 7/2001 | Burbank |
| 6,264,676 B1 | 7/2001 | Gellman |
| 6,270,475 B1 | 8/2001 | Bestetti |
| 6,283,949 B1 | 9/2001 | Roorda |
| 6,316,734 B1 | 11/2001 | Yang |

(56) References Cited

U.S. PATENT DOCUMENTS

| | | |
|---|---|---|
| 6,321,124 B1 | 11/2001 | Cigaina |
| 6,349,740 B1 | 2/2002 | Cho |
| 6,432,040 B1 | 8/2002 | Meah |
| 6,447,550 B1 | 9/2002 | Hunter |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent |
| 6,572,587 B2 | 6/2003 | Lerman |
| 6,589,184 B2 | 7/2003 | Noren |
| 6,648,849 B2 | 11/2003 | Tenhuisen |
| 6,666,845 B2 | 12/2003 | Hooper |
| 6,689,100 B2 | 2/2004 | Connelly |
| 6,723,053 B2 | 4/2004 | Ackerman |
| 6,733,519 B2 | 5/2004 | Lashinski |
| 6,792,309 B1 | 9/2004 | Noren |
| 6,810,880 B1 | 11/2004 | Jennings |
| 6,813,964 B1 | 11/2004 | Clark |
| 6,860,857 B2 | 3/2005 | Noren |
| 6,915,162 B2 | 7/2005 | Noren |
| 6,921,267 B2 | 7/2005 | van Oostrom et al. |
| 6,929,631 B1 | 8/2005 | Brugger |
| 6,939,299 B1 | 9/2005 | Petersen |
| 6,953,444 B2 | 10/2005 | Rosenberg |
| 6,964,204 B2 | 11/2005 | Clark |
| 6,966,875 B1 | 11/2005 | Longobardi |
| 6,997,914 B2 | 2/2006 | Smith |
| 7,017,583 B2 | 3/2006 | Forsell |
| 7,020,531 B1 | 3/2006 | Colliou |
| 7,056,286 B2 | 6/2006 | Ravenscroft |
| 7,063,669 B2 | 6/2006 | Brawner |
| 7,073,387 B2 | 7/2006 | Zdeblick |
| 7,082,843 B2 | 8/2006 | Clark |
| 7,118,693 B2 | 10/2006 | Glatkowski |
| 7,131,945 B2 | 11/2006 | Fink |
| 7,144,400 B2 | 12/2006 | Byrum |
| 7,149,587 B2 | 12/2006 | Wardle |
| 7,191,007 B2 | 3/2007 | Desai |
| 7,195,774 B2 | 3/2007 | Carvalho |
| 7,223,239 B2 | 5/2007 | Schulze |
| 7,226,419 B2 | 6/2007 | Lane |
| 7,261,003 B2 | 8/2007 | McDonald |
| 7,267,645 B2 | 9/2007 | Anderson |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum |
| 7,351,226 B1 | 4/2008 | Herskowitz |
| 7,351,240 B2 | 4/2008 | Hassler |
| 7,353,747 B2 | 4/2008 | Swayze |
| 7,364,542 B2 | 4/2008 | Jambor |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,413,547 B1 | 8/2008 | Lichtscheidl |
| 7,416,528 B2 | 8/2008 | Crawford |
| 7,437,951 B2 | 10/2008 | McDonald |
| 7,438,718 B2 | 10/2008 | Milliman |
| 7,445,614 B2 | 11/2008 | Bunodiere |
| 7,468,038 B2 | 12/2008 | Ye |
| 7,500,944 B2 | 3/2009 | Byrum |
| 7,510,530 B2 | 3/2009 | Hashimoto |
| 7,530,943 B2 | 5/2009 | Lechner |
| 7,553,298 B2 | 6/2009 | Hunt |
| 7,561,916 B2 | 7/2009 | Hunt |
| 7,563,255 B2 | 7/2009 | Adamis |
| 7,580,746 B2 | 8/2009 | Gilkerson |
| 7,591,185 B1 | 9/2009 | Mothilal |
| 7,593,777 B2 | 9/2009 | Gerber |
| 7,634,319 B2 | 12/2009 | Schneider |
| 7,651,483 B2 | 1/2010 | Byrum |
| 7,658,196 B2 | 2/2010 | Ferreri |
| 7,699,770 B2 | 4/2010 | Hassler |
| 7,708,722 B2 | 5/2010 | Glenn |
| 7,762,998 B2 | 7/2010 | Birk |
| 7,762,999 B2 | 7/2010 | Byrum |
| 7,775,215 B2 | 8/2010 | Hassler |
| 7,775,966 B2 | 8/2010 | Dlugos |
| 7,811,275 B2 | 10/2010 | Birk |
| 7,850,660 B2 | 12/2010 | Uth |
| 7,862,546 B2 | 1/2011 | Conlon |
| 7,909,754 B2 | 3/2011 | Hassler |
| 7,909,804 B2 | 3/2011 | Stats |
| 8,007,474 B2 | 8/2011 | Uth |
| 2001/0052141 A1 | 12/2001 | Andersen |
| 2002/0013545 A1 | 1/2002 | Soltanpour |
| 2002/0058969 A1 | 5/2002 | Noren |
| 2002/0087147 A1 | 7/2002 | Hooper |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren |
| 2003/0045910 A1 | 3/2003 | Sorensen |
| 2003/0073880 A1 | 4/2003 | Polsky |
| 2003/0078506 A1 | 4/2003 | Noren |
| 2003/0139690 A1 | 7/2003 | Aebli |
| 2003/0194710 A1 | 10/2003 | Yang |
| 2004/0064110 A1 | 4/2004 | Forsell |
| 2004/0065615 A1 | 4/2004 | Hooper |
| 2004/0068233 A1 | 4/2004 | DiMatteo |
| 2004/0082908 A1 | 4/2004 | Whitehurst |
| 2004/0111050 A1 | 6/2004 | Smedley |
| 2004/0127807 A1* | 7/2004 | Hatlesad et al. ............... 600/529 |
| 2004/0204692 A1 | 10/2004 | Eliasen |
| 2004/0213951 A1 | 10/2004 | Shimokawa |
| 2004/0254536 A1 | 12/2004 | Conlon |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0010177 A1 | 1/2005 | Tsai |
| 2005/0049578 A1 | 3/2005 | Tu |
| 2005/0070875 A1 | 3/2005 | Kulessa |
| 2005/0070937 A1 | 3/2005 | Jambor |
| 2005/0085778 A1 | 4/2005 | Parks |
| 2005/0092093 A1 | 5/2005 | Kang |
| 2005/0131325 A1 | 6/2005 | Chen |
| 2005/0131352 A1 | 6/2005 | Conlon |
| 2005/0131383 A1 | 6/2005 | Chen |
| 2005/0148956 A1 | 7/2005 | Conlon |
| 2005/0149143 A1 | 7/2005 | Libbus |
| 2005/0209573 A1 | 9/2005 | Brugger |
| 2005/0240155 A1 | 10/2005 | Conlon |
| 2005/0240156 A1 | 10/2005 | Conlon |
| 2005/0244453 A1 | 11/2005 | Stucke |
| 2005/0267500 A1 | 12/2005 | Hassler |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2006/0074439 A1 | 4/2006 | Garner |
| 2006/0122578 A1 | 6/2006 | Lord |
| 2006/0161186 A1 | 7/2006 | Hassler |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron |
| 2006/0184141 A1 | 8/2006 | Smith |
| 2006/0189887 A1 | 8/2006 | Hassler |
| 2006/0189888 A1 | 8/2006 | Hassler |
| 2006/0190039 A1 | 8/2006 | Birk |
| 2006/0199997 A1 | 9/2006 | Hassler |

(56) References Cited

U.S. PATENT DOCUMENTS

| | | |
|---|---|---|
| 2006/0211912 A1 | 9/2006 | Dlugos |
| 2006/0211913 A1 | 9/2006 | Dlugos |
| 2006/0211914 A1 | 9/2006 | Hassler |
| 2006/0217668 A1 | 9/2006 | Schulze |
| 2006/0217673 A1 | 9/2006 | Schulze |
| 2006/0225274 A1 | 10/2006 | Greenberg |
| 2006/0235445 A1 | 10/2006 | Birk |
| 2006/0235448 A1 | 10/2006 | Roslin |
| 2006/0247539 A1 | 11/2006 | Schugt |
| 2006/0266128 A1 | 11/2006 | Clark |
| 2006/0293625 A1 | 12/2006 | Hunt |
| 2006/0293626 A1 | 12/2006 | Byrum |
| 2006/0293627 A1 | 12/2006 | Byrum |
| 2006/0293628 A1 | 12/2006 | Hunt |
| 2007/0010790 A1 | 1/2007 | Byrum |
| 2007/0015954 A1 | 1/2007 | Dlugos |
| 2007/0015955 A1 | 1/2007 | Tsonton |
| 2007/0016231 A1 | 1/2007 | Jambor |
| 2007/0027356 A1 | 2/2007 | Ortiz |
| 2007/0038255 A1 | 2/2007 | Kieval |
| 2007/0060959 A1 | 3/2007 | Salo |
| 2007/0073250 A1 | 3/2007 | Schneiter |
| 2007/0078391 A1 | 4/2007 | Wortley |
| 2007/0088336 A1 | 4/2007 | Dalton |
| 2007/0088391 A1 | 4/2007 | McAlexander |
| 2007/0129765 A1 | 6/2007 | Gilkerson |
| 2007/0135758 A1 | 6/2007 | Childers |
| 2007/0149947 A1 | 6/2007 | Byrum |
| 2007/0156013 A1* | 7/2007 | Birk ............................ 600/37 |
| 2007/0158769 A1 | 7/2007 | You |
| 2007/0160743 A1 | 7/2007 | Babitt |
| 2007/0161958 A1 | 7/2007 | Glenn |
| 2007/0167672 A1 | 7/2007 | Dlugos |
| 2007/0173685 A1 | 7/2007 | Jambor |
| 2007/0185462 A1 | 8/2007 | Byrum |
| 2007/0191717 A1 | 8/2007 | Rosen |
| 2007/0205384 A1 | 9/2007 | Kurosawa |
| 2007/0208313 A1 | 9/2007 | Conlon |
| 2007/0213837 A1* | 9/2007 | Ferreri et al. ........... 623/23.65 |
| 2007/0219510 A1 | 9/2007 | Zinn |
| 2007/0235083 A1 | 10/2007 | Dlugos |
| 2007/0238992 A1* | 10/2007 | Donofrio et al. ............ 600/437 |
| 2007/0250086 A1 | 10/2007 | Wiley |
| 2007/0255165 A1 | 11/2007 | Uesugi |
| 2007/0255234 A1 | 11/2007 | Haase |
| 2007/0265645 A1 | 11/2007 | Birk |
| 2007/0265666 A1 | 11/2007 | Roberts |
| 2007/0282196 A1 | 12/2007 | Birk |
| 2007/0293829 A1 | 12/2007 | Conlon |
| 2008/0009680 A1 | 1/2008 | Hassler |
| 2008/0015406 A1 | 1/2008 | Dlugos |
| 2008/0039772 A1 | 2/2008 | Chantriaux |
| 2008/0058632 A1 | 3/2008 | Tai |
| 2008/0097496 A1 | 4/2008 | Chang |
| 2008/0114308 A1 | 5/2008 | di Palma et al. |
| 2008/0119798 A1 | 5/2008 | Chantriaux |
| 2008/0243093 A1 | 10/2008 | Kalpin |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0281412 A1 | 11/2008 | Smith |
| 2008/0287969 A1 | 11/2008 | Tsonton |
| 2008/0287974 A1 | 11/2008 | Widenhouse |
| 2008/0312553 A1 | 12/2008 | Timmons |
| 2008/0319435 A1 | 12/2008 | Rioux |
| 2009/0018608 A1 | 1/2009 | Schwartz |
| 2009/0048524 A1 | 2/2009 | Wildau |
| 2009/0054914 A1 | 2/2009 | Lechner |
| 2009/0062825 A1 | 3/2009 | Pool |
| 2009/0071258 A1 | 3/2009 | Kouda |
| 2009/0076466 A1 | 3/2009 | Quebbemann |
| 2009/0082757 A1 | 3/2009 | Rogers |
| 2009/0082793 A1 | 3/2009 | Birk |
| 2009/0093768 A1 | 4/2009 | Conlon |
| 2009/0099538 A1 | 4/2009 | Paganon |
| 2009/0105735 A1 | 4/2009 | Stam |
| 2009/0112308 A1 | 4/2009 | Kassem |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1 | 8/2009 | Coe |
| 2009/0221974 A1 | 9/2009 | Paganon |
| 2009/0222031 A1 | 9/2009 | Axelsson |
| 2009/0222065 A1 | 9/2009 | Dlugos |
| 2009/0227862 A1 | 9/2009 | Smith |
| 2009/0228028 A1 | 9/2009 | Coe |
| 2009/0228072 A1 | 9/2009 | Coe |
| 2009/0234273 A1* | 9/2009 | Intoccia et al. ............... 604/22 |
| 2009/0234302 A1* | 9/2009 | Hoendervoogt et al. 604/288.01 |
| 2009/0248125 A1 | 10/2009 | Brostrom |
| 2009/0248126 A1 | 10/2009 | Nippoldt |
| 2009/0254052 A1 | 10/2009 | Birk |
| 2009/0259190 A1 | 10/2009 | Birk |
| 2009/0259191 A1 | 10/2009 | Birk |
| 2009/0259231 A1 | 10/2009 | Birk |
| 2009/0264901 A1 | 10/2009 | Franklin |
| 2009/0270904 A1 | 10/2009 | Birk |
| 2009/0299216 A1 | 12/2009 | Chen |
| 2009/0299672 A1 | 12/2009 | Zhang |
| 2009/0306462 A1 | 12/2009 | Lechner |
| 2009/0308169 A1 | 12/2009 | Mothilal |
| 2009/0317443 A1 | 12/2009 | Willis |
| 2010/0087843 A1 | 4/2010 | Bertolote |
| 2010/0100079 A1 | 4/2010 | Berkcan |
| 2010/0114149 A1 | 5/2010 | Albrecht |
| 2010/0130941 A1 | 5/2010 | Conlon |
| 2010/0152532 A1 | 6/2010 | Marcotte |
| 2010/0191271 A1 | 7/2010 | Lau |
| 2010/0211085 A1 | 8/2010 | Uth |
| 2010/0217198 A1 | 8/2010 | Franklin |
| 2010/0217199 A1 | 8/2010 | Uth |
| 2010/0217200 A1 | 8/2010 | Uth |
| 2010/0228080 A1 | 9/2010 | Tavori |
| 2010/0234808 A1 | 9/2010 | Uth |
| 2010/0286766 A1 | 11/2010 | Ye |
| 2011/0054407 A1 | 3/2011 | Olroyd |
| 2011/0082426 A1 | 4/2011 | Conlon |

FOREIGN PATENT DOCUMENTS

| | | |
|---|---|---|
| DE | 3927001 | 2/1991 |
| DE | 4211045 | 10/1993 |
| DE | 19745654 | 4/1999 |
| DE | 19751791 | 5/1999 |
| EP | 0343910 A2 | 11/1989 |
| EP | 0611561 | 8/1994 |
| EP | 0858814 | 8/1998 |
| EP | 0867197 | 9/1998 |
| EP | 1057457 | 12/2000 |
| EP | 1346753 | 9/2003 |
| EP | 1396242 A1 | 3/2004 |
| EP | 1396243 A1 | 3/2004 |
| EP | 1488824 A1 | 12/2004 |
| EP | 1543861 A1 | 6/2005 |

(56) References Cited

FOREIGN PATENT DOCUMENTS

| | | |
|---|---|---|
| EP | 1547643 | 6/2005 |
| EP | 1591140 A1 | 11/2005 |
| EP | 1736194 A1 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 A1 | 6/2009 |
| EP | 2095798 | 9/2009 |
| FR | 2740977 | 5/1997 |
| FR | 2797181 A1 | 2/2001 |
| FR | 2823663 A1 | 10/2002 |
| FR | 2851168 | 8/2004 |
| FR | 2855744 A1 | 12/2004 |
| FR | 2916980 | 12/2008 |
| JP | 2119877 | 5/1990 |
| JP | 8107934 | 4/1996 |
| SU | 1823791 | 6/1991 |
| WO | 9220519 A1 | 11/1992 |
| WO | 9422520 | 10/1994 |
| WO | 9640357 | 12/1996 |
| WO | 9701370 | 1/1997 |
| WO | 9920338 | 4/1999 |
| WO | 9926543 | 6/1999 |
| WO | 9934859 | 7/1999 |
| WO | 0015158 A1 | 3/2000 |
| WO | 0033901 | 6/2000 |
| WO | 0110359 A1 | 2/2001 |
| WO | 0149245 A2 | 7/2001 |
| WO | 0180926 | 11/2001 |
| WO | 0195813 A1 | 12/2001 |
| WO | 0210667 A2 | 2/2002 |
| WO | 02074381 | 9/2002 |
| WO | 03105732 A1 | 12/2003 |
| WO | 2004016971 | 2/2004 |
| WO | 2005037055 A2 | 4/2005 |
| WO | 2005072627 A1 | 8/2005 |
| WO | 2006021695 | 3/2006 |
| WO | 2009007526 | 1/2009 |
| WO | 2009129474 A1 | 10/2009 |

OTHER PUBLICATIONS

Autumn K. et al.; 'Evidence of Van Der Waals Adhesion in Gecko Setae'; PNAS; vol. 99; No. 19; pp. 12252-12256; Sep. 17, 2012.

Geim AK. et al.; 'Microfabricated Adhesive Mimicking Gecko Foot-Hair'; Nature Materials Abstract only; vol. 2; No. 7; 2003.

Yamagami, Takuji; 'Technical Developments; Use of Targeting Guide Wire in Left Subclavian Puncture During Percutaneous Implantation of Port-Catheter Systems Using the Catheter Tip Fixation Method' European Radiology; vol. 13; pp. 863-866; 2003.

Yurdumakan B., et al.; 'Synthetic Gecko Foot-Hairs from Multiwalled Carbon Nanotubes'; The Royal Society of Chemistry; p. 3799-3801; 2005.

\* cited by examiner

ELECTRONICALLY ENHANCED ACCESS PORT FOR A FLUID FILLED IMPLANT

RELATED APPLICATIONS

This application is a continuation of U.S. patent application Ser. No. 12/873,096, filed Aug. 31, 2010, which claims priority to and the benefit of U.S. Provisional Patent Application No. 61/330,266, filed on Apr. 30, 2010, the entire disclosures of which are incorporated herein by reference.

FIELD

The present invention broadly relates to gastric bands and more specifically, to an electronically enhanced access port for a gastric band.

BACKGROUND

There are numerous varieties of fluid filled surgical implants presently comprising, or which may in the future comprise, access ports, for hydraulically adjustable gastric bands.

An exemplary hydraulic adjustable gastric band comprises a saline solution inside of one or more inflatable portions (e.g., silicone shells) positioned on the stomach surface of the ring of the gastric band to adjust the gastric band through a variety of diameters. As the inflatable portion is inflated it reduces the stoma of the gastric band and when the inflatable portion is deflated it increases the stoma of the gastric band. The saline solution is added to or removed from the inflatable portion via an access port fixed beneath the skin of the patient in the abdomen on the rectus muscle sheath using a fine needle to find the right level of restriction.

An exemplary gastric band (hydraulic, hydraulic-mechanical hybrid, or otherwise) may additionally, or alternatively, comprise an access port coupled with an override mechanism to rapidly remove fluid or gel from the implant in the event of an emergency.

Each of the foregoing implants, as well as others, comprise access ports that may be candidates for various electronics based enhancements, e.g., an access port fitted with a pressure sensor and/or an access port that transmits a signal for easier detection of its location within the body of the patient.

By way of example of the latter, it is essential with a hydraulic adjustable gastric band that the orientation of the implanted access port allows fluidic contact with the Huber needle of the syringe. In other words, the septum of the implanted access port should ideally be parallel to the plane defined by the surface of the patient's skin above the septum of the implanted access port. However, it is possible for the implanted access port to tilt from the ideal orientation resulting in less surface area for fluidic contact with the Huber needle. Thus, there is a need for tilt detection, communication, and compensation for fluid filled surgical implants.

Ferreri et al. (U.S. Pat. No. 7,658,196) discloses a system operable to detect the orientation of an implant component. Ferreri discloses that a sense head can be moved around a patient's body to determine a location of the implanted access port using, for example, triangulation. However, Ferreri does not disclose that the tilt detection occurs at the sense head by moving a sense head to a location of the center of the port. Thus, a user must scan a large area of the patient's body in order to determine the tilt of the implanted access port. This can be embarrassing to the patient, and inconvenient to the patient, and/or time consuming.

SUMMARY

In accordance with exemplary embodiments, the present invention provides for an electronically enhanced access port for a fluid filled implant. The access port may be used to connect to an implanted medical device, such as, a gastric band for the treatment of obesity, the gastric band may be suitable for laparoscopic placement around the stomach of a patient to create a stoma.

In accordance with exemplary embodiments, the present invention provides for an access port configured to detect the pressure of a fluid within the implant. In accordance with other exemplary embodiments, the present invention provides for an access port configured to detect its location within the body to facilitate a physician's access thereto.

In one embodiment, the present invention is an access port for a gastric band including a penetrable septum, a conduit configured to provide fluid communication between the penetrable septum and the gastric band, and an electronics based enhancement. The electronics based enhancement may be a pressure sensor or a tilt detector.

In another embodiment, the present invention is an access port for a gastric band including a penetrable septum, a conduit configured to provide fluid communication between the penetrable septum and the gastric band, and a pressure sensor in fluid communication with a fluid within the gastric band and configured to monitor a pressure of the fluid, generate a pressure value signal, and communicate the pressure value signal to an external control unit via RF telemetry.

In still another embodiment, the present invention is an access port for a gastric band including a penetrable septum, a conduit configured to provide fluid communication between the penetrable septum and the gastric band, and a tilt detector configured to detect a tilt datum indicating a tilt direction of the access port relative to body portions of the patient and a degree tilt of the access port relative to a surface of a skin of the patient.

BRIEF DESCRIPTION OF THE DRAWINGS

The exemplary embodiments of the present invention will be described in conjunction with the accompanying drawing FIGS. in which like numerals denote like elements and.

DETAILED DESCRIPTION

In accordance with exemplary embodiments, the present invention comprises an electronically enhanced access port for a gastric band. Persons skilled in the art will readily appreciate that various aspects of the present invention may be realized by any number of methods and devices configured to perform the intended functions. Stated differently, other methods and devices may be incorporated herein to perform the intended functions. It should also be noted that the drawing FIGS. referred to herein are not all drawn to scale, but may be exaggerated to illustrate various aspects of the invention, and in that regard, the drawing FIGS. should not be construed as limiting. Finally, although the present invention may be described in connection with various medical principles and beliefs, the present invention should not be bound by theory.

By way of example, the present invention will be described primarily with reference to hydraulically adjustable gastric bands. Nevertheless, persons skilled in the art will readily appreciate that the present invention advantageously may be applied to one of the numerous varieties of fluid filled surgical implants presently comprising, or which may in the future comprise, access ports. Similarly, while the present invention will be described primarily with reference to fluid filled surgical implants, persons skilled in the art will readily appreciate that the present invention advantageously may be applied to other devices, and whether fluid or gel filled.

In accordance with exemplary embodiments, the present invention provides for an access port configured to detect the pressure of a fluid within the implant.

At the outset, it should be noted that while the present invention will be described primarily with reference to an access port, persons skilled in the art will readily appreciate that an access port is not necessary for detection of the pressure of a fluid within an implant. Stated differently, the diagnostic and therapeutic advantages associated with knowing the pressure of a fluid within an implant, as provided for by the present invention, may be realized without fluid access to the implant via an access port.

In exemplary embodiments, an access port comprises a sensor. The sensor can be in communication with an implant and configured to monitor a parameter of the access port. For example, the access port can be in communication with the fluid in the implant and can generate a pressure value signal based on the parameter and one or more parameter control limits. The parameter can be, for example, a pressure, a fill volume, a stress, a strain, a linear measurement of the implant, a force of the implant on the patient, and combinations thereof. The implant can be, for example, a gastric band.

In exemplary embodiments, the pressure sensor is coupled with a printed circuit board assembly (PCBA), which is in turn configured to telemetrically relay (e.g., via RF) a pressure value signal generated by the pressure sensor to an external control unit.

In exemplary embodiments, the pressure sensor and the PCBA are inductively powered, e.g., using an external magnetic field. In other embodiments, the pressure sensor and the PCBA are powered by one or more of a battery, rechargeable or otherwise, a capacitor, or a fuel cell. In accordance with various aspects of an exemplary embodiment, the power source is recharged by one or more of motion, a chemical change, or a temperature change. For example, in exemplary embodiments, the pressure sensor and the PCBA are powered by one or more of the following: (i) kinetic energy created by body motion stored onto a capacitor, (ii) an implanted fuel cell, (iii) an implanted power source powered by chemistry of the body, (iv) an implanted power source powered by temperature change, and (v) implanted batteries that can be recharged by direct contact or inductive coupling.

In exemplary embodiments, the pressure sensor, the PCBA and the power source are co-housed, while in other embodiments, they are separately housed. By way of non-limiting examples, a hermetically sealed, self contained package may contain the PCBA and the power source, while a package comprising the pressure sensor, and necessary electronics and signal conditioning, can relay a pressure value signal to a separate package comprising the PCBA for conversion to an RF signal and telemetric relay to an external control unit. In this manner, the PCBA may be in direct contact with the fluid within the access port and the implant.

In accordance with one aspect of an exemplary embodiment, an access port comprising a pressure sensor further comprises an element structurally and/or spatially configured to guard the pressure sensor against a needle damaging it. In exemplary embodiments, the element is positioned between the access port septum and the pressure sensor, but other spatial configurations are contemplated. In exemplary embodiments, the element is housed separately from the PCBA so as to not interfere with telemetric relay of the RF signal to an external control unit.

Exemplary materials comprise titanium, stainless steel, ceramic and the like. That being said, persons skilled in the art will readily appreciate that any material which, by virtue of its thickness and/or hardness, is capable of guarding the pressure sensor against the needle damaging the pressure sensor, is suitable for use herein.

Figure 1A:
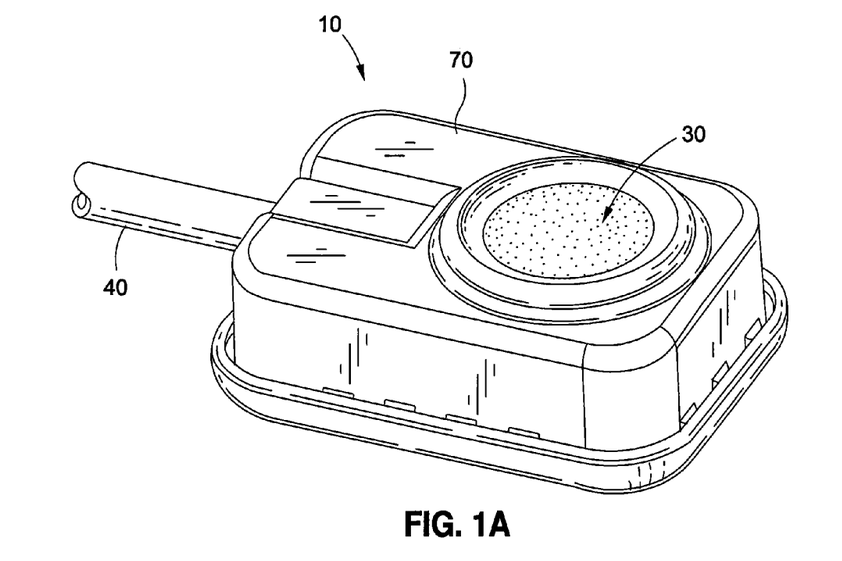
FIG. 1A illustrates an access port comprising a pressure sensor in accordance with an exemplary embodiment.
Figure 1B:
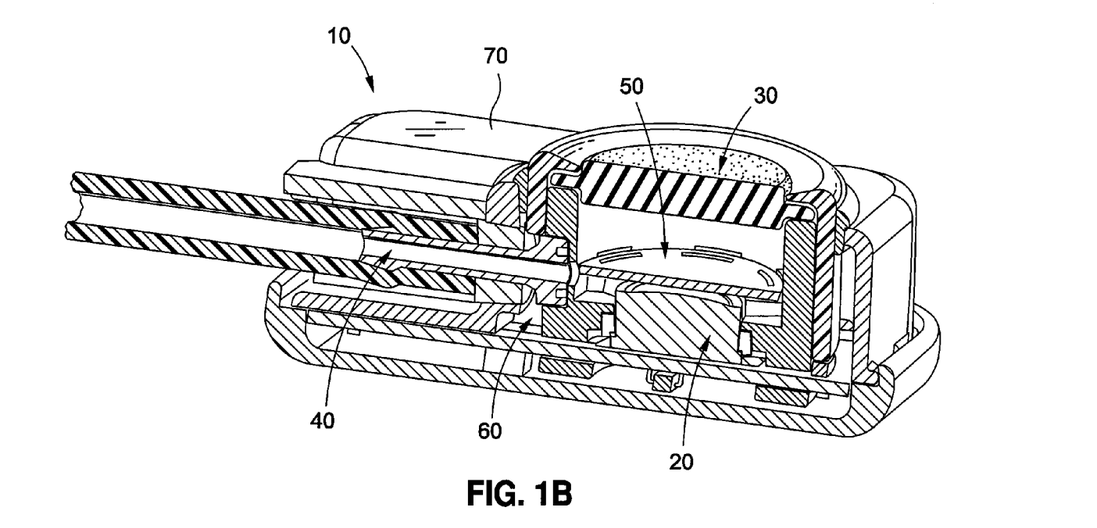
FIG. 1B illustrates a cross sectional view of an access port comprising a pressure sensor in accordance with an exemplary embodiment.

Turning now to FIGS. 1A and 1B, an exemplary access port 10 comprising a pressure sensor 20 is depicted. The access port 10 comprises a penetrable septum 30 through which fluid or gel is added to or removed from the access port 10 using a needle, and is thereby added to or removed from the fluid filled implant via a conduit 40. The needle can be, for example, a fine needle, a Huber needle, or any other type of needle which can supply fluid or gel to the access port 10. In addition, a tube, instead of a needle can be used. The access port 10 can be connected, for example, to a gastric band (not shown) and can be used to supply or remove fluid or gel from the gastric band. The access port 10 can also be connected, for example, to a breast implant (not shown) and can be used to supply or remove fluid or gel from the breast implant. In this embodiment, a plate element 50 is positioned between the penetrable septum 30 and the pressure sensor 20. The positioning of the plate element 50 serves to prevent the needle from damaging the pressure sensor 20. The plate element 50 can be formed, for example, from titanium, stainless steel, or any other type of material that can protect the pressure sensor 20 from damage.

The PCBA 60 can be connected, for example, to the pressure sensor 20. The PCBA 60 is configured to telemetrically relay a pressure value obtained from the pressure sensor 20 to an external control unit. The pressure value can indicate, for example, a pressure of the access port 10 and/or the gastric band. The pressure sensor 20 can also detect, for example, a fill volume, a strain, and/or a linear measurement of the access port 10. The access port 10 can also include, for example, a housing 70 which can, for example, define a cavity containing the pressure sensor 20, a portion of the conduit 40, the plate element 50, and/or the PCBA 60. The penetrable septum 30 can define, for example, an outer wall of the housing 70.

In accordance with exemplary embodiments, the present invention provides for an access port configured to detect its location within the body to facilitate a physician's access thereto. The location can be, for example, a relative location, or an exact location. In one embodiment, the access port 10 can be configured to determine the orientation of the implanted access port relative to the surface of the skin when a patient is in a known position, such as laying supine or standing vertically.

In exemplary embodiments, the access port 10 is configured to detect a tilt orientation of less than about 15 degrees, more preferably less than about 5 degrees, and most preferably less than about 1 degree.

In accordance with exemplary embodiments, the present invention utilizes electronics in the implanted access port and an external control unit to inductively power and control the implanted access port. In other embodiments, the implanted access port is powered by one or more of a battery, rechargeable or otherwise, a capacitor, and/or a fuel cell. In accordance with various aspects of an exemplary embodiment, the power source is recharged by one or more of motion, a chemical change, or a temperature change. For example, in exemplary embodiments, the implanted access port is powered by one or more of the following: (i) kinetic energy created by body motion stored onto a capacitor, (ii) an implanted fuel cell, (iii) an implanted power source powered by chemistry of the body, (iv) an implanted power source powered by temperature change, and/or (v) implanted batteries that can be recharged by direct contact or inductive coupling.

In accordance with exemplary embodiments, the external control unit uses RF telemetry to query the implanted access port for tilt information and then displays this information. Examples of display information are graphical, alpha-numeric such as a measure of tilt orientation in degrees, textual such as "flipped" versus "OK," or a combination of these forms.

Once the tilt of the implanted access port relative to the surface of the skin above the implanted access port is known, then contacting the implanted access port with the Huber needle at a similarly matching tilt may, in some embodiments, help to compensate for the reduced surface area of the septum as compared to the ideal implanted access port orientation. Another embodiment of tilt compensation may be to manipulate the port by hand to reposition it closer to the ideal orientation. The following FIGS. illustrate tilt detection, communication, and compensation for exemplary implanted access port orientations.

Figure 2A:
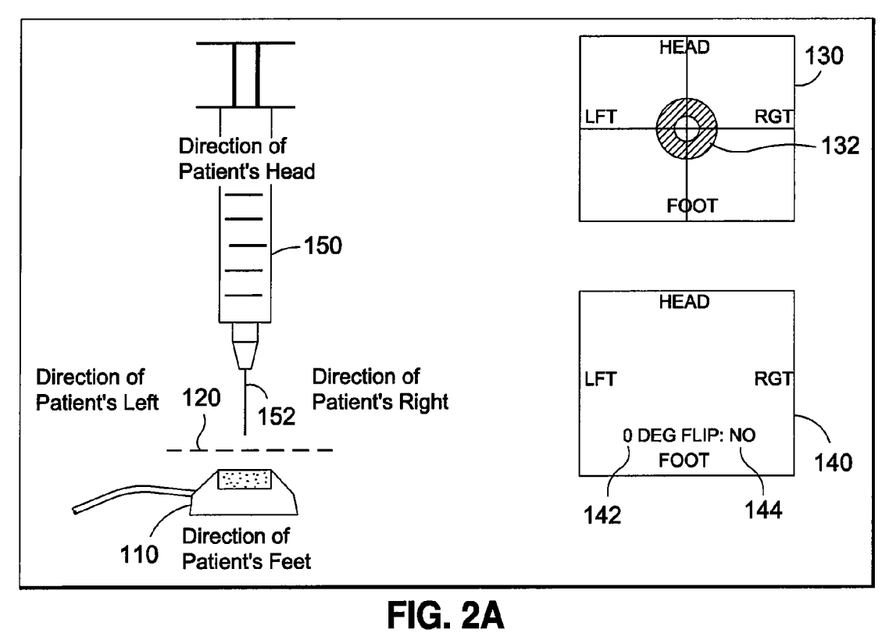
FIGS. 2A-2D illustrate tilt detection, communication, and compensation for exemplary implanted access port orientations in accordance with an exemplary embodiment.

FIG. 2A illustrates an implanted access port 110 oriented substantially parallel to a plane defined by the surface of the patient's skin 120 above the implanted access port 110. FIG. 2A also depicts a syringe 150 and a needle 152 of the syringe 150. The needle 152 can be, for example, a Huber needle. Also shown are exemplary graphical and alpha-numeric displays 130 and 140, respectively, for an external control unit (not shown) in accordance with exemplary embodiments. In one embodiment, a tilt detector may be located within the implanted access port 110 and/or the external control unit to determine tilt datum indicating the tilt of the implanted access port 110. The tilt detector and/or the tilt datum can aid, for example, in generating the alpha-numeric displays 130 and 140. The alpha-numeric display 130 can indicate, for example, a relative location of the implanted access port 110.

The alpha-numeric display 130 can include, for example, an icon 132. The icon 132 can indicate, for example, a tilt direction of the implanted access port 110 relative to body portions of the patient and a degree tilt of the implanted access port 110 relative to a surface of a skin of the patient. The degree tilt can be, for example, an amount of tilt of the implanted access port 110. The tilt direction can be indicated by the location of the icon 132 relative to an intersection of the lines in the alpha-numeric display 130. For example, angular measurements of the location of the tilt direction relative to the intersection of the lines in the alpha-numeric display 130 can indicate that the implanted access port 110 is tilted in a direction of the head of the patient, the left side of the patient, the right side of the patient, or the foot. The icon 132 can also indicate the degree tilt of the implanted access port 110 through the location of the icon 132 relative to the intersection of the lines in the alpha-numeric display 130. For example, the magnitude of the distance between the icon 132 and the intersection of the lines in the alpha-numeric display can indicate a degree tilt of the implant access port 110. The icon 132 can also indicate whether the implanted access port 110 is non-flipped, or whether it has flipped.

In the non-flipped (or correct) position, a penetrable septum of the implanted access port 110 is facing or partially facing the skin 120. In the flipped position, the penetrable septum is not facing the skin 120 such that it is not possible to contact the penetrable septum with the needle. While the orientation of the access port can sometimes be ascertained simply by sense of touch or the more involved use of fluoroscopy, there have been cases where a flipped port cannot be positively identified even with fluoroscopy. In FIG. 2A, the icon 132 indicates that the implanted access port 110 is not tilted. The white center in the icon 132 also indicates that the implanted access port 110 is in a non-flipped position.

Furthermore, the alpha-numeric display 140 can also include a degree indication 142 and a flipped indication 144. The degree indication 142 can digitally numerically indicate, for example, a degree tilt of the implanted access port 110. The flipped indication 144 can give, for example, an indication as to whether the implanted access port 110 has flipped or not. In FIG. 2A, the degree indication 142 indicates a 0 degree tilt while the flipped indication 144 indicates that the implanted access port 110 has not flipped. Thus, in FIG. 2A, no compensation with the syringe 150 and/or the needle 152 is required.

Figure 2B:
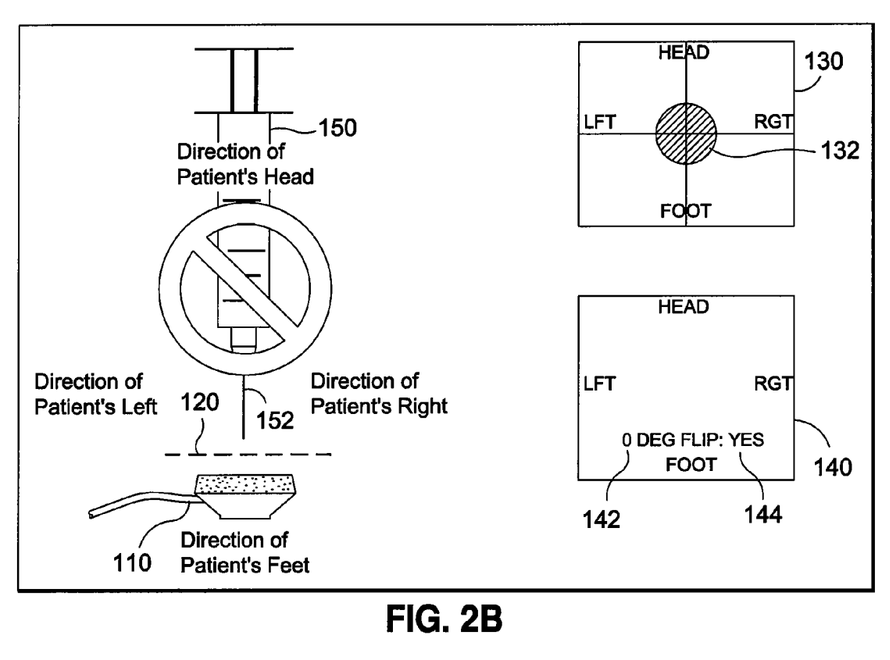

FIG. 2B therefore illustrates an implanted access port 110 flipped relative to the plane defined by the surface of the patient's skin 120 above the implanted access port 110. Again shown are exemplary graphical and alpha-numeric displays 130 and 140, respectively, for an external control unit in accordance with exemplary embodiments. The degree indication 142 indicates that the implanted access port 110 has no tilt relative to the surface of the skin. The icon 132 in FIG. 2B is located at the intersection indicating no magnitude for the degree tilt, and thus indicates that the implanted access port 110 is not tilted. However, the lack of the white center in the icon 132 indicates that the implanted access port 110 has flipped. This is also confirmed by the flipped indication 144 indicating that the implanted access port 110 has flipped. In FIG. 2B, no compensation with the syringe 150 and/or the needle 152 is sufficient since the access port must be flipped back to its non-flip state before the syringe 150 and/or the needle 152 can be used to access the implanted access port 110.

Figure 2C:
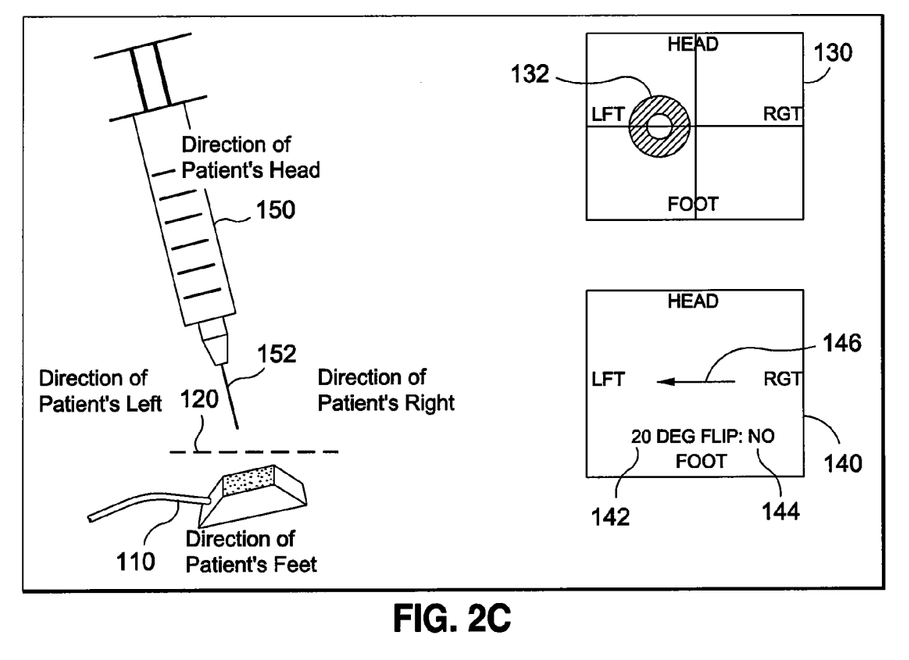

FIG. 2C illustrates an implanted access port 110 tiled to the patient's left relative to the plane defined by the surface of the patient's skin 120 above the implanted access port 110. Again shown are exemplary graphical and alpha-numeric displays 130 and 140, respectively, for an external control unit in accordance with exemplary embodiments. In FIG. 2C, the icon 132 indicates that the implanted access port 110 is tilted in a direction to the left side of the patient's body at an approximately 20 degree angle. The 20 degree angle can be estimated based on the distance between the icon 132 and the intersection of the lines in the alpha-numeric display 130. The icon 132 also indicates that the implanted access port 110 has not flipped. This is confirmed, for example, by the flipped indication 144, which states that the implanted access port 110 has not flipped. Furthermore, in FIG. 2C, an arrow 146 in the alpha-numeric display 140 further indicates the tilt direction of the implanted access port 110. Here, the arrow 146 is pointed directly to the left indicating that the implanted access port is tilted towards a left side of the patient. The degree indication 142 also indicates that the implanted access port 110 is tilted at a 20 degree angle. Thus, compensation of approximately 20 degrees to the left side of the patient with the syringe 150 and/or the needle 152 is needed.

Figure 2D:
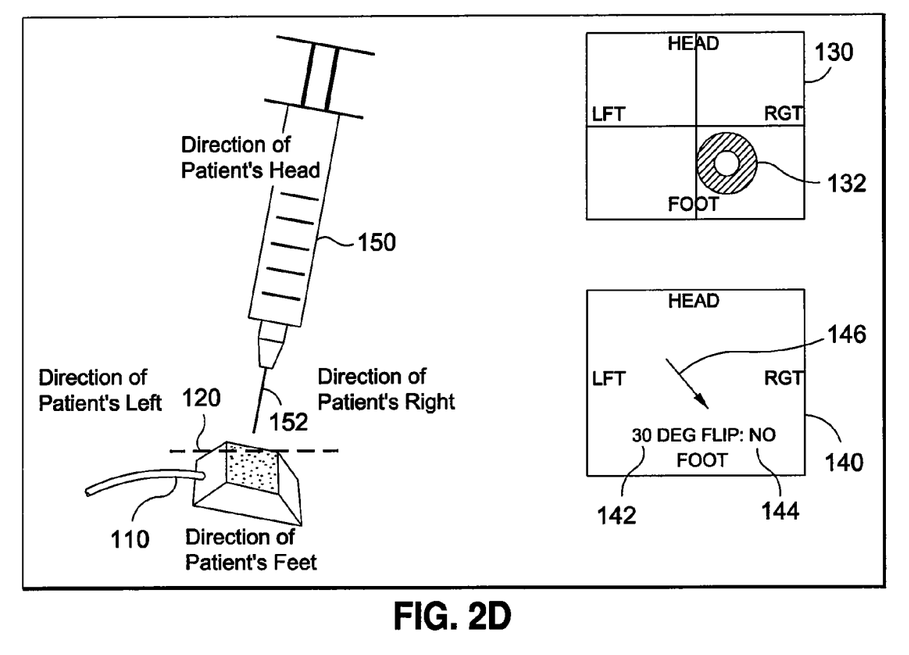

FIG. 2D illustrates an implanted access port 110 tiled to the patient's feet and right relative to the plane defined by the surface of the patient's skin 120 above the implanted access port 110. Also shown are exemplary graphical and alpha-numeric displays, 130 and 140, respectively, for an external control unit in accordance with exemplary embodiments. In FIG. 2D, the icon 132 indicates that the implanted access port 110 is tilted towards the right side of the patient's body and the patient's foot. Based on the distance between the icon 132 and the intersection of the lines in the alpha-numeric display 130, a degree tilt of 30 degrees relative to the surface of the skin of the patient can be estimated. The icon 132 indicates that the implanted access port 110 is not flipped. This is confirmed, for example, by the arrow 146 and the flipped indication 144. Furthermore, the degree indication 142 digitally numerically indicates that the implanted access port 110 is tilted at a 30 degree angle. Thus, compensation of approximately 30 degrees generally to the right side of the patient's body and the patient's foot with the syringe 150 and/or the needle 152 is needed.

Figure 3A:
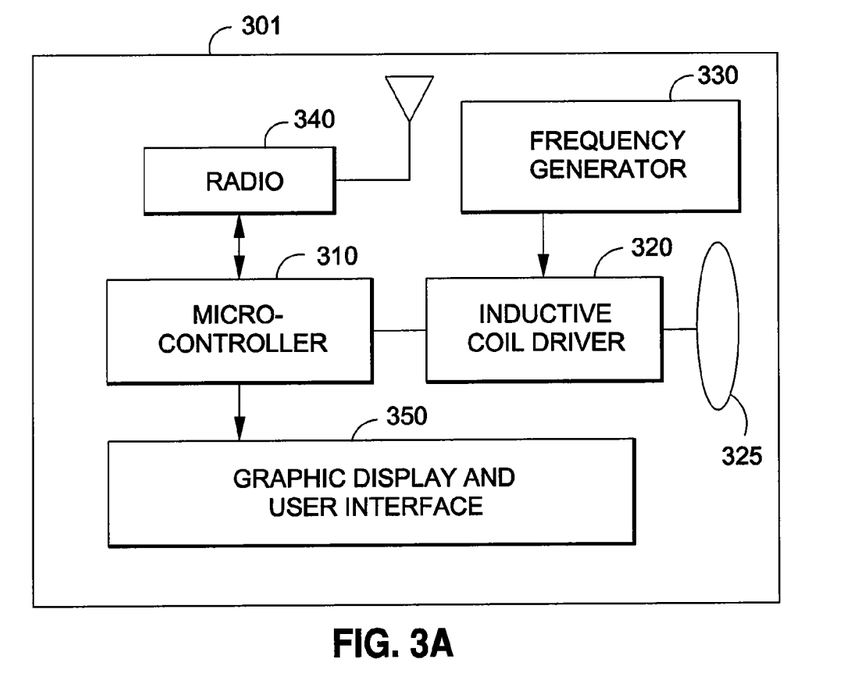
FIG. 3A illustrates the components of an external control unit in accordance with an exemplary embodiment.
Figure 3B:
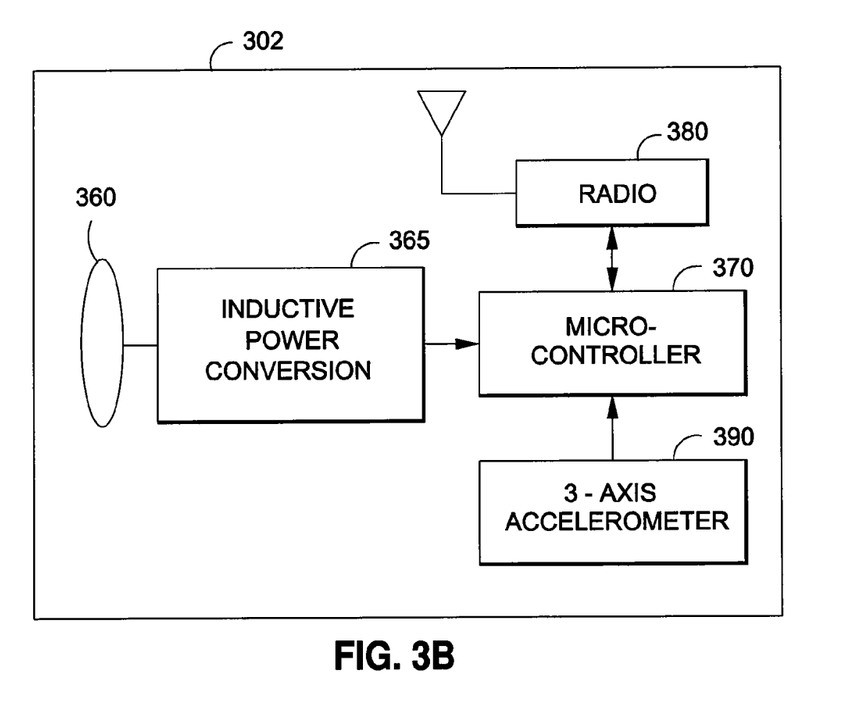
FIG. 3B illustrates the components of an implanted access port in accordance with an exemplary embodiment.

With reference now to FIGS. 3A and 3B, an exemplary external control unit 301 comprises a micro-controller 310 that manages the various functions of the external control unit 301. The micro-controller 310 interfaces to an inductive coil driver 320 that sends RF energy to an exemplary implanted access port 302 via a loop antenna 325. The inductive coil driver 320 in exemplary embodiments comprises semiconductor switches such as transistors or field effect transistors, and it drives a coil that is tuned to the proper frequency using RF tuning capacitors. A frequency generator 330 creates the proper frequency for the inductive coil driver 320. An RF radio 340 passes data to and from the micro-controller 310 and communicates with a matching implanted access port RF radio 380.

A graphic display and user interface 350 are connected to the micro-controller 310 and provide information to and from the operator of the external control unit 301. The graphic display is, in an exemplary embodiment, a color touch screen liquid crystal display (LCD). The user interface is, in an exemplary embodiment, also a color touch screen LCD, and may further comprise buttons, voice recognition, buzzer, speaker, switches, keyboard, trackball, touch tablet, and other similar human interface devices.

Turning now to FIG. 3B, the implanted access port 302 comprises an inductive coil tuned circuit, further comprising a loop antenna 360 and low loss RF tuning capacitors that supply power to an inductive power conversion circuit 365. The inductive power conversion circuit 365 transforms the input RF energy to DC energy for use by the implanted access port 302 electronics utilizing a bridge rectifier, filtering capacitors, and a voltage regulator. It is also possible to use an implanted battery or other external or internal energy source. Typical inductive powering RF frequencies can be approximately 125 kHz, 6.75 MHz, or 27 MHz. The voltage regulator can be a switch mode power supply or linear regulator depending on voltage levels and efficiency requirements. Typical voltage levels can range from 1 volt to 20 volts. The inductive power conversion circuit 365 in exemplary embodiments has one or more protection mechanisms such as over temperature and over voltage shut down.

A micro-controller 370 is used to execute software that performs the various functions of the implanted access port 302. Examples of suitable micro-controllers 370 are the Texas Instrument® MSP430 or CC430 series, Atmel AT32 L series, Freescale Coldfire series, and similar commercially available devices.

The RF radio 380 interfaces with the micro-controller 370 to transmit and receive data to and from the external control unit 301. A preferred frequency range for RF radio 380 is in the Medical Implant Communications Service (MICS) frequency band of approximately 402 MHz to 405 MHz. Examples of applicable radio devices are the Texas Instruments® CC1101, Atmer ATA542X series, Microchip MRF49XA, and similar commercially available devices. The micro-controller 370 monitors the input voltage to ensure that it is within a predetermined range and communicates with external control unit 301 if changes to the input voltage of the implanted access port 302 are necessary. Furthermore, the micro-controller 370 in the implanted access port 302 can communicate with the micro-controller 310 in the control unit 301 to increase or decrease an amount of energy supplied to the implanted access port 302 in order to maintain optimal operating conditions. Such monitoring can occur at regular intervals.

A 3-axis accelerometer 390 can be used to sense a tilt of the implanted access port 302 based on its orientation relative to gravity and interfaces to the micro-controller 370 to provide tilt information. Examples of the 3-axis accelerometer 390 are the Analog Devices ADXL335, Freescale MMA7660FC, and similar commercially available devices.

In exemplary embodiments, the implanted access port 302 is contained within a housing. In one embodiment, the external control unit 301 and/or the implanted access port 302 can detect when a syringe and/or a needle of the syringe has contacted the implanted access port 302. For example, the implanted access port 302 can detect vibration data and transmit such vibration data to the external control unit 301. The external control unit 301 can analyze the vibration data to determine whether the vibration data indicates that the syringe and/or the needle of the syringe has contacted the implanted access port 302.

In another embodiment, the external control unit 301 and/or the implanted access port 302 can detect when the syringe and/or the needle of the syringe has entered or been inserted into the implanted access port 302. For example, a user can move the syringe and/or the needle of the syringe when it is believed to have entered the implanted access port 302. The user can then see if a corresponding tilt of the implanted access port 302 is displayed on the external control unit 301. If tilting the syringe and/or needle of the syringe causes the implanted access port 110 to tilt, then it is likely that the syringe and/or the needle of the syringe is inserted into the implanted access port 110. However, if tilting the syringe and/or the needle of the syringe does not cause the implanted access port 110 to tilt, then it is likely that the syringe and/or the needle of the syringe is not inserted into the implanted access port 110.

In exemplary embodiments, in order to accurately and precisely measure the tilt angle, the implanted access port 110 is implanted in the same orientation each time. Otherwise, head-to-foot and right-to-left references may be incorrect. In other exemplary embodiments, the patient may be asked to roll to the right, then roll to the left, then sit up, all from a supine position while "training" the external control unit to learn the implanted access port tilt directions. In yet other exemplary embodiments, only whether the implanted access port has flipped is measured by the implanted access port 110.

Figure 4A:
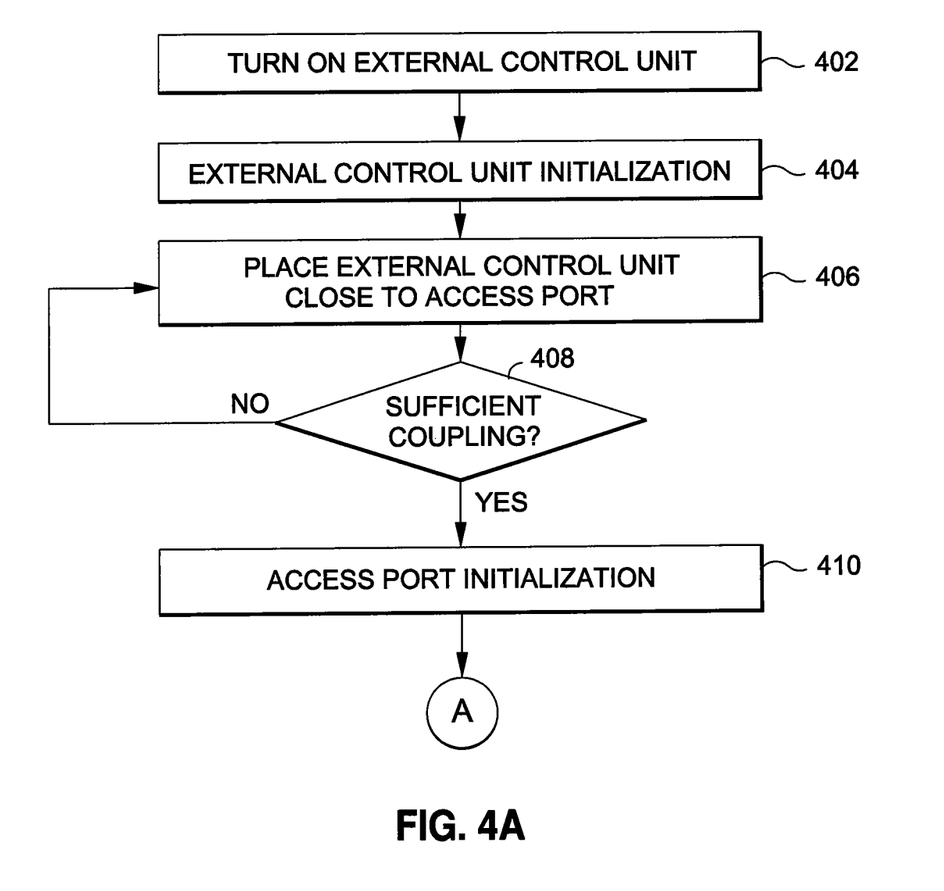
FIGS. 4A and 4B illustrate an exemplary method of tilt detection and communication in accordance with an exemplary embodiment.
Figure 4B:
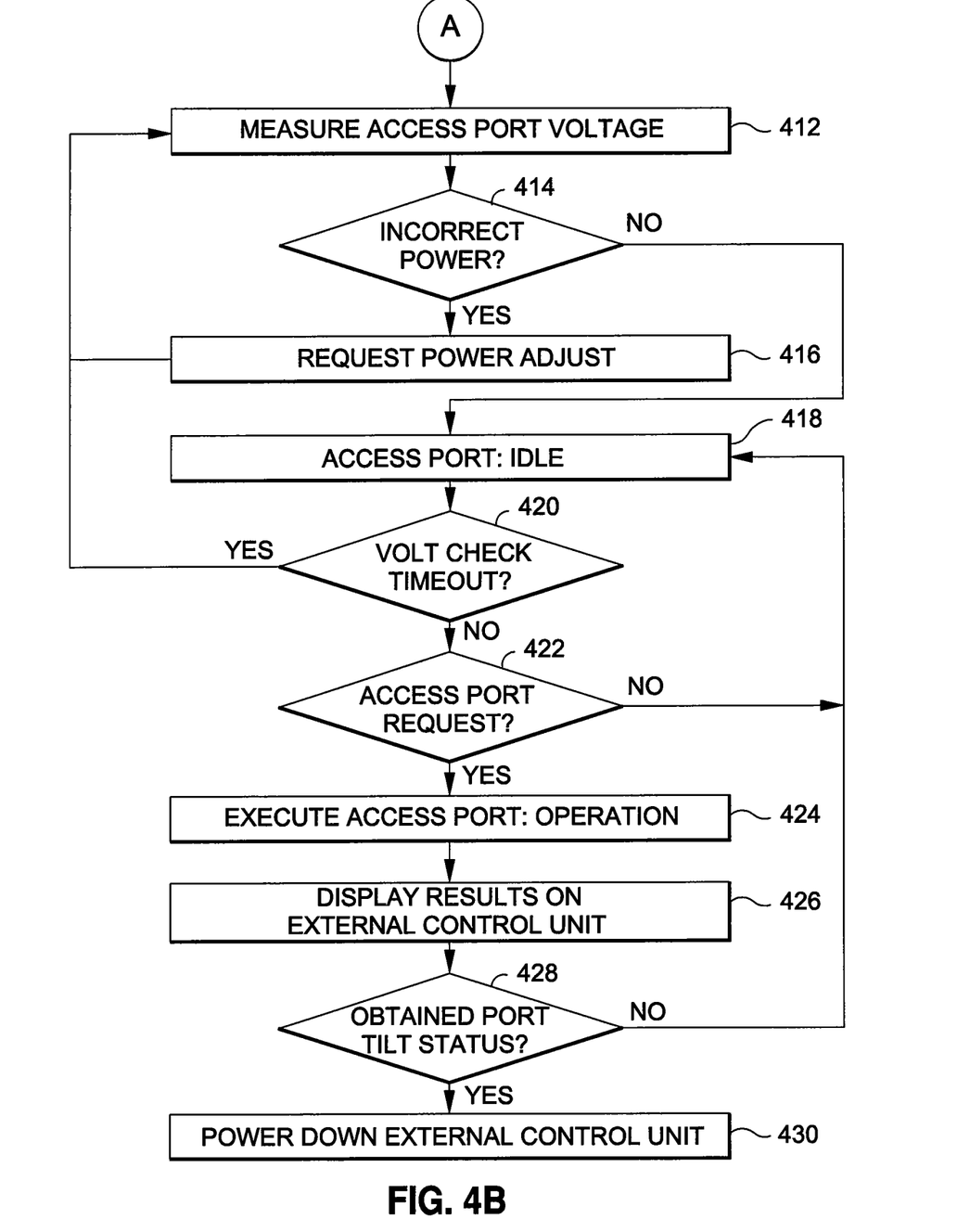

FIGS. 4A and 4B depict an exemplary method of tilt detection and communication. First, the physician turns on the external control unit (step 402). The external control unit in turn initializes (step 404) and informs the physician to place the external control unit inductive coil next to the patient's implanted access port (step 406). Once there is sufficient inductive energy coupling between the external control unit and the implanted access port (step 408), the implanted access port signals the external control unit that it is powered up along with any other identifying, diagnostic, initialization, or other such information (step 410). It is possible that too much or too little energy can be coupled so the implanted access port monitors this condition (step 412) and if there is an incorrect power (step 414), a radio link can be used to communicate with the external control unit to decrease or increase the coil drive (step 416). In exemplary embodiments, the voltage monitoring function occurs at regular intervals to maintain optimal operating conditions (step 420).

After the optimal operating conditions have been established, the tilt information from the implanted access port is passed to and displayed on the external control unit (step 426). The communication protocol to pass tilt information between the implanted access port and the external control unit can be implemented in any practical form. For example, one embodiment is to have the implanted access port stay in a low power, or idle mode (step 418) and go to initialization, diagnostics, tilt measurement, voltage measurement, temperature measurement, radio communication or other higher power modes (step 424) only when requested to do so by the external control unit (step 422). This communication protocol is advantageous because the implanted access port is primarily in a low power, or idle mode thereby minimizing implant heating. Another embodiment is to have the implanted access port go to initialization, diagnostics, tilt measurement, voltage measurement, temperature measurement, radio communication or other higher power modes only at regular intervals determined by the implanted access port.

At this point, the physician can act on implanted access port tilt information that has been conveyed through the external control unit (step 428). If the implanted access port is within a reasonable tilt angle, access thereto can proceed normally. However, if the implanted access port indicates that it is in a flipped position, then the physician can act accordingly such as further analysis by fluoroscopy. The external control unit is finally powered down (step 430).

Advantageously the present invention allows a determination of whether the access port 110 has flipped without resorting to the inherent risks of ionizing radiation, potentially error prone interpretation, and time consuming process of fluoroscopy. In addition, the reporting of the tilt angle allows for an adjustment of the angle of the access port 110 and/or the Huber needle in order to compensate for the associated reduction in exposed septum area.

Figure 5:
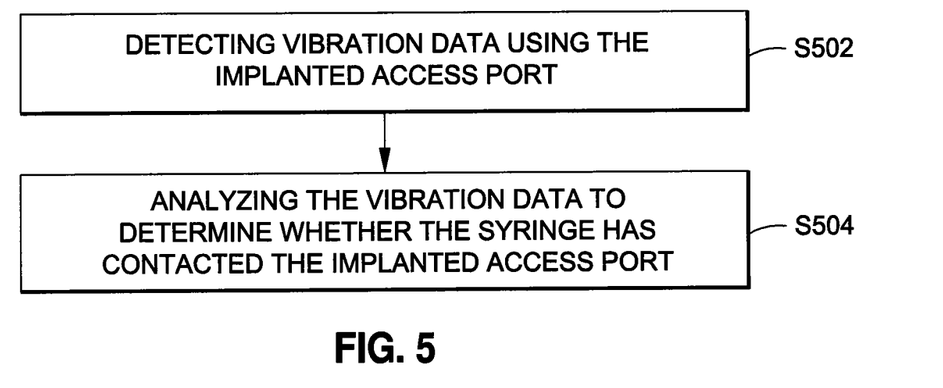
FIG. 5 illustrates a process in accordance with an exemplary embodiment.

In one embodiment, the present invention is a process shown in FIG. 5. In Step S502, vibration data is detected using the implanted access port. For example, the implanted access port 302 can detect vibration data and transmit such vibration data to the external control unit 301. In Step S504, the vibration data can be analyzed to determine whether the syringe has contacted the implanted access port. For example, the external control unit 301 can analyze the vibration data to determine whether the vibration data indicates that the syringe and/or the needle of the syringe has contacted the implanted access port 302.

Figure 6:
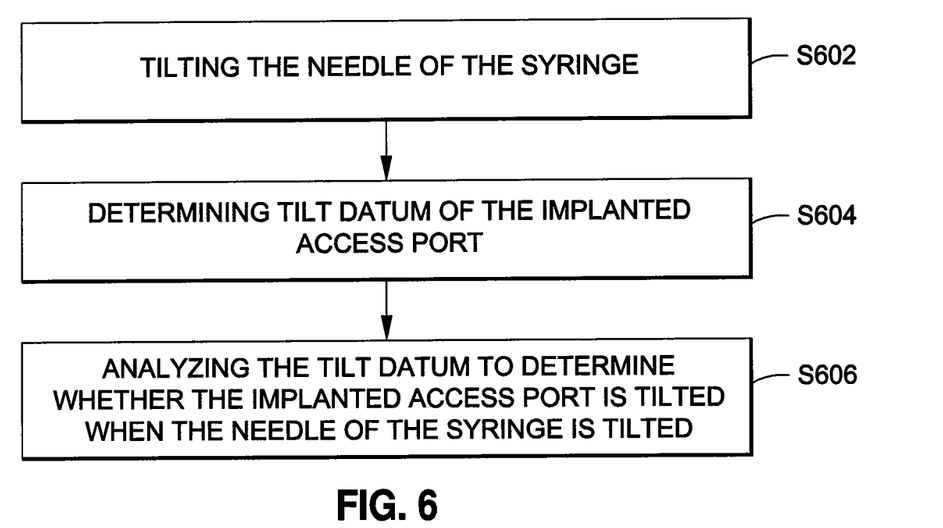
FIG. 6 illustrates a process in accordance with an exemplary embodiment.

In another embodiment, the present invention is a process shown in FIG. 6. In Step S602, a needle of the syringe is tilted. For example, a user can move the syringe and/or the needle of the syringe when it is believed to have entered the implanted access port 302. In Step S604, tilt datum of the implanted access port is determined. For example, the tilt datum of the implanted access port 302 can be analyzed.

In Step S606, the tilt datum is analyzed to determine whether the implanted access port is tilted when the needle of the syringe is tilted. For example, the user can then see if a corresponding tilt of the implanted access port 302 is displayed on the external control unit 301. If tilting the syringe and/or the needle of the syringe causes the implanted access port 110 to tilt, then it is likely that the syringe and/or the needle of the syringe is inserted into the implanted access port 110. However, if tilting the syringe and/or the needle of the syringe does not cause the implanted access port 110 to tilt, then it is likely that the syringe and/or the needle of the syringe is not inserted into the implanted access port 110.

The foregoing disclosure is illustrative of the present invention and is not to be construed as limiting the invention. Although one or more embodiments of the invention have been described, persons skilled in the art will readily appreciate that numerous modifications could be made without departing from the spirit and scope of the present invention. It should be understood that all such modifications are intended to be included within the scope of the invention.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An access port for connecting to a gastric band for the treatment of obesity, the gastric band suitable for laparoscopic placement around the stomach of a patient to create a stoma, the access port comprising:
    a housing defining a cavity and comprising a penetrable septum defining an outer wall of the housing;
    a conduit configured to carry fluid between the penetrable septum and an inflatable portion of the gastric band; and
    a tilt detector coupled to the housing and configured to determine a tilt direction of the housing relative to at least one body portion of the patient including head, left side, right side, and foot, and to detect whether or not the housing is flipped away from the surface of the skin of the patient, wherein an external control unit is configured to communicate with the tilt detector and, based on the communication, the external control unit is configured to display a tilt datum and an indicator of whether or not the housing is tilted in a direction of at least one of the patient's head, left side, right side, and foot.

2. The access port of claim 1, wherein the tilt detector is a 3-axis accelerometer.

3. The access port of claim 1, wherein the gastric band is a hydraulically adjustable gastric band.

4. The access port of claim 1, wherein the tilt detector is further configured to communicate the tilt datum to the external control unit via RF telemetry.

5. The access port of claim 1, wherein the tilt detector is powered by kinetic energy created by body motion stored onto a capacitor.

6. The access port of claim 1, wherein the tilt detector is powered by an implanted fuel cell.

7. The access port of claim 1, wherein the tilt detector is powered by an implanted power source powered by chemistry of the body.

8. The access port of claim 1, wherein the tilt detector is powered by an implanted power source powered by temperature change.

9. The access port of claim 1, wherein the tilt detector is powered by implanted batteries that can be recharged by direct contact.

10. The access port of claim 1, wherein the tilt detector is inductively powered.

11. The access port of claim 1, further comprising a sensor located in the housing, the sensor detecting a parameter.

12. The access port of claim 11, wherein the parameter is selected from a group consisting of a pressure, a fill volume, a stress, a strain, a linear measurement, and combinations thereof.

13. The access port of claim 11, wherein the sensor is a pressure sensor.

14. The access port of claim 13, further comprising a plate element positioned between the penetrable septum and the pressure sensor to guard the pressure sensor against a needle damaging it.

15. An access port for connecting to a gastric band for the treatment of obesity, the gastric band suitable for laparoscopic placement around the stomach of a patient to create a stoma, the access port comprising:
    a penetrable septum defining an outer wall of a housing;
    a conduit configured to carry fluid between the penetrable septum and an inflatable portion of the gastric band; and
    a tilt detector coupled to the housing and configured to detect a tilt direction of the housing relative to at least one body portion of the patient including head, left side, right side, and foot, and to detect a degree tilt of the housing relative to a surface of a skin of the patient, and to detect whether or not the housing is flipped away from the surface of the skin of the patient, wherein an external control unit is configured to communicate with the tilt detector and, based on the communication, the external control unit is configured to display a tilt datum and an indicator of whether or not the housing is tilted in a direction of at least one of the patient's head, left side, right side, and foot.

16. The access port of claim 15, further comprising a pressure sensor in fluid communication with a fluid within the gastric band and configured to monitor a pressure of the fluid and generate a pressure value signal.

17. An access port for connecting to a gastric band for the treatment of obesity, the gastric band suitable for laparoscopic placement around the stomach of a patient to create a stoma, the access port comprising:
    a penetrable septum defining an outer wall of a housing;
    a conduit configured to provide fluid communication between the penetrable septum and the gastric band; and
    a tilt detector coupled to the housing and configured to detect a tilt datum indicating a tilt direction of the access port relative to at least one body portion of the patient including head, left side, right side, and foot, and a degree tilt of the access port relative to a surface of a skin of the patient, and to detect whether or not the housing is flipped away from the surface of the skin of the patient, wherein an external control unit is configured to communicate with the tilt detector and, based on the communication, the external control unit is configured to display a tilt datum and an indicator of whether or not the housing is tilted in a direction of at least one of the patient's head, left side, right side and foot.

18. The access port of claim 17, wherein the external control unit is configured to receive via RF telemetry the tilt datum and a location of the access port and to display the tilt datum and a location of the access port.

19. The access port of claim 17, wherein the tilt detector is a 3-axis accelerometer.

20. A method of determining an insertion of a needle of a syringe into an implanted access port comprising:

providing an external control unit to wirelessly communicate with the implanted access port through tissue of a patient in which the access port is implanted;
inserting the needle of the syringe into a patient;
tilting the inserted needle of the syringe;
determining, with the external control unit, a tilt datum of the implanted access port;
analyzing, with the external control unit, the tilt datum to determine whether the implanted access port is tilted in response to tilting the needle of the syringe;
determining, with the external control unit, that the needle of the syringe is inserted into the access port if it is determined that the access port is tilted in response to tilting the needle of the syringe; and
determining, with the external control unit, that the needle of the syringe is not inserted into the access port if it is determined that the access port is not tilted in response to tilting the needle of the syringe.

21. A system for determining an insertion of a needle of a syringe into an implanted access port comprising:
an implanted access port having a housing defining a cavity, the housing comprising a penetrable septum defining an outer wall of the housing and a tilt detector coupled to the housing and configured to determine a tilt direction of the housing relative to at least one body portion of the patient; and
an external control unit in wireless communication with the implanted access port, the external control unit comprising a processor and a non-transitory processor-readable storage medium storing a program for causing the processor to execute a method for determining an insertion of a needle of a syringe into the implanted access port, the method comprising:
wirelessly communicating with the implanted access port through tissue of a patient in which the access port is implanted and in which the needle of the syringe is inserted into a patient;
determining a tilt datum of the implanted access port based on data received from the implanted access port;
analyzing the tilt datum to determine whether the implanted access port is tilted in response to tilting the needle of the syringe;
determining that the needle of the syringe is inserted into the access port if it is determined that the access port is tilted in response to tilting the needle of the syringe; and
determining that the needle of the syringe is not inserted into the access port if it is determined that the access port is not tilted in response to tilting the needle of the syringe.

* * * * *